US008685388B2

(12) United States Patent
Veiga et al.

(10) Patent No.: US 8,685,388 B2
(45) Date of Patent: Apr. 1, 2014

(54) METHOD FOR REDUCING GASTRO-INTESTINAL INFLAMMATION USING *BIFIDOBACTERIUM ANIMALIS* BACTERIA OR A FERMENTED DAIRY PRODUCT COMPRISING SUCH BACTERIA

(75) Inventors: Patrick Veiga, Suresnes (FR); Isabelle Chambaud, Issy Les Moulineaux (FR); Artem Khlebnikov, New Rochelle, NY (US); Laurie H. Glimcher, Newton, MA (US); Wendy S. Garrett, Brookline, MA (US)

(73) Assignees: Compagnie Gervais Danone, Paris (FR); President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 13/505,088

(22) PCT Filed: Nov. 2, 2009

(86) PCT No.: PCT/IB2009/056007
§ 371 (c)(1),
(2), (4) Date: Aug. 14, 2012

(87) PCT Pub. No.: WO2011/051760
PCT Pub. Date: May 5, 2011

(65) Prior Publication Data
US 2012/0308523 A1    Dec. 6, 2012

(51) Int. Cl.
*A01N 63/00*    (2006.01)
*A01N 65/00*    (2009.01)
(52) U.S. Cl.
USPC ........................................ 424/93.3; 424/93.1
(58) Field of Classification Search
None
See application file for complete search history.

(56) References Cited

U.S. PATENT DOCUMENTS

2008/0206233 A1*  8/2008  Frenken et al. ............ 424/130.1
2009/0110663 A1   4/2009  Halow
2009/0238796 A1   9/2009  Maculevich et al.

FOREIGN PATENT DOCUMENTS

EP         2 072 053 A1       6/2009
WO    WO 2007009568 A1 *    1/2007    ............... A23C 9/12

OTHER PUBLICATIONS

Guyonnet D. et al., "Effect of a fermented milk containing *Bifidobacterium animalis* DN-173 010 on the health-related quality of life and symptoms in irritable bowel syndrome in adults in primary care: a multicentre, rendomized, double-blind, controlled trial" Alimentary Pharmacology & Therapeutics, Blackwell Scientific Publications LTD., Cambridge, (2007), vol. 26 (3) pp. 475-486.
Guyonnet D. et al., "Fermented milk containing *Bifidobacterium lactis* DN-173 010 improved self-reported digestive comfort amongst a general population of adults. A randomized, open-label, controlled, pilot study." Journal of Digestive Disease (2009), vol. 10 (1) pp. 61-70.
O'Mahony et al., "*Lactobacillus* and *Bifidobacterium* in irritable bowel syndrome: Symptom responses and relationship to cytokine profiles" Gastroenterology (2005), vol. 128(3), pp. 541-551.

* cited by examiner

*Primary Examiner* — Chris R Tate
*Assistant Examiner* — Douglas F White
(74) *Attorney, Agent, or Firm* — McDonnell Boehnen Hulbert & Berghoff LLP

(57) ABSTRACT

The present invention relates to a method for the prevention, treatment and reduction of gastro-intestinal inflammation in a subject by administering a specific *Bifidobacterium* bacteria, in particular a fermented dairy product comprising said specific *Bifidobacterium* bacteria for the prevention, treatment and reduction of gastro-intestinal inflammation, in particular for the prevention and treatment of inflammatory bowel disease (IBD), ulcerative colitis (UC) and/or Crohn's Disease (CD) and for the prevention and treatment of Irritable Bowel Syndrome (IBS).

15 Claims, 4 Drawing Sheets

US 8,685,388 B2

METHOD FOR REDUCING GASTRO-INTESTINAL INFLAMMATION USING *BIFIDOBACTERIUM ANIMALIS* BACTERIA OR A FERMENTED DAIRY PRODUCT COMPRISING SUCH BACTERIA

INTRODUCTION

The present invention relates to a method for the prevention, treatment and reduction of gastro-intestinal inflammation in a subject by administering a specific *Bifidobacterium* strain, in particular a fermented dairy product comprising said specific *Bifidobacterium* strain for the prevention, treatment and reduction of gastro-intestinal inflammation, in particular for the prevention and treatment of inflammatory bowel disease (IBD), ulcerative colitis (UC) and/or Crohn's Disease (CD) and for the prevention and treatment of Irritable Bowel Syndrome (IBS).

BACKGROUND

The gastro-intestinal lumen is massively colonized by bacteria and for most metazoans this relationship is mutually beneficial. The epithelial cell barrier is essential for the symbiosis of prokaryotes and eukaryotic hosts, as it creates a boundary necessary for coexistence by preventing mucosal inflammation in response to bacterial or other luminal stimuli. However, in some individuals this balance is upset, resulting in persistent gastro-intestinal inflammation (IBD), that manifests itself in two major diseases, Crohn's disease and ulcerative colitis (UC), and may well also contribute to Irritable Bowel Syndrome (IBS).

Garrett et al. (Communicable ulcerative colitis induced by T-bet deficiency in the innate immune system. *Cell* 131, 33-45 (2007)) have developed a robust mouse model of ulcerative colitis whose pathologic features and response to anti-TNF treatment closely resemble the human disease. It was found that deficiency of a particular regulatory gene in the innate immune system (resulting from a double knock out of the genes T-bet & RAG2; named TRUC for T-bet RAG2 Ulcerative Colitis) resulted in aggressive, spontaneous, and communicable UC and increased susceptibility to colitis in immunologically intact hosts. The pathogenesis of the disease was mapped to the excessive production of the pro-inflammatory cytokine, TNF-α in dendritic cells in the colon. The mucosal immune system displayed a hyperactive response by overproducing TNF-α in colonic dendritic cells, a cytokine that is cytotoxic for gastro-intestinal epithelial cells. The ensuing breach of the colonic epithelial barrier led to a shift in the commensal bacterial population to a colitogenic flora. This colitogenic flora could then be transmitted both vertically and horizontally to genetically intact hosts.

DETAILED DESCRIPTION OF THE INVENTION

Surprisingly, using the robust mouse model as described above, it was now found that gastro-intestinal inflammation in a subject could be decreased by administering a fermented dairy product comprising the probiotic strain *Bifidobacterium animalis* subsp *lactis* DN 173 010, more in particular the commercially available (ex Danone S.A.) fermented probiotic preparation called Activia®, comprising said *Bifidobacterium animalis* subsp *lactis* DN 173 010 strain.

According to one embodiment, the invention is concerned with the reduction of gastro-intestinal inflammation in a subject in need thereof by administering to said subject an effective amount of the *Bifidobacterium animalis* subsp *lactis* strain DN-173010. The *Bifidobacterium animalis* subsp *lactis* strain DN-173010 has been deposited under the number 1-2494 at CNCM on Jun. 20, 2000. This strain is known under the code DN-173 010 and is protected, with its use as glycosylation modulator of gastro-intestinal cell surface, by European Patent EP 1 297 176.

*Bifidobacterium animalis* is a Gram-positive anaerobic rod-shaped bacterium, which can be found in the large intestines of most mammals, including humans. *Bifidobacterium animalis* and were previously described as two distinct species. Presently, both are considered *Bifidobacterium animalis* with the subspecies *animalis* and *lactis*, respectively. Both old names *Bifidobacterium animalis* and *Bifidobacterium lactis* are still used on product labels, as this species is frequently used as a probiotic. In the context of this invention, the names *Bifidobacterium lactis* and *Bifidobacterium animalis* subsp *lactis* may be used interchangeably.

According to another embodiment, the invention is concerned with the reduction of gastro-intestinal inflammation in a subject in need thereof by administering to said subject an effective amount of a fermented dairy product comprising said specific strain *Bifidobacterium animalis* subsp *lactis* DN-173010.

According to a specific embodiment, said fermented dairy product further comprises two classical yoghurt starters, the lactic acid bacteria *Streptococcus thermophilus* and *Lactobacillus bulgaricus*. Although the term Activia® is a proprietary brand name of Danone S.A., the term will be used in this application to indicate a fermented dairy product comprising the probiotic strain *Bifidobacterium animalis* subsp *lactis* DN-173 010 together with a strain of *S. thermophilus* and a strain of *L. bulgaricus*.

According to one embodiment, the strain *Bifidobacterium animalis* subsp *lactis* DN-173010, deposited under the number CNCM 1-2494, or the fermented product according to the invention is administered during at least 14 days, preferably during at least 21 days, more preferably during at least 28 days.

According to one embodiment, the strain *Bifidobacterium animalis* subsp *lactis* DN-173010, deposited under the number CNCM 1-2494, or the fermented product according to the invention is administered in an amount of at least $10^3$ cfu per intake, preferably between $10^3$ and $10^{12}$ cfu per intake, more preferably between $10^6$ and $10^{11}$ per intake, most preferably at about $10^{10}$ cfu per intake.

According to one embodiment, the strain *Bifidobacterium animalis* subsp *lactis* DN-173010, deposited under the number CNCM 1-2494, or the fermented product according to the invention is administered in an amount of at least $10^3$ cfu per intake, preferably between $10^3$ and $10^{11}$ cfu per intake, more preferably between $10^6$ and $10^{12}$ per intake, most preferably at about $10^{10}$ cfu per intake, two times per day during at least 14 days, preferably during at least 21 days, more preferably during at least 28 days.

According to one embodiment, the strain *Bifidobacterium animalis* subsp *lactis* DN-173010, deposited under the number CNCM 1-2494 is administered as a pharmaceutical composition, further combined with a pharmaceutically acceptable carrier, which may comprise excipients.

According to one embodiment, the pharmaceutical composition also comprises at least one other agent active against IBD or IBS.

The term "pharmaceutical composition" is intended to mean "drug" or "OTC (Over The Counter)".

According to another embodiment, the fermented dairy product comprising said strain *Bifidobacterium animalis* subsp *lactis* DN-173010, deposited under the number CNCM 1-2494 is administered as a yoghurt.

According to one embodiment, the invention is concerned with a method for the prevention, treatment and reduction of gastro-intestinal inflammation in a subject by administering said strain *Bifidobacterium animalis* subsp *lactis* DN-173010, deposited under the number CNCM 1-2494, in particular a fermented dairy product comprising said strain *Bifidobacterium animalis* subsp *lactis* DN-173010, deposited under the number CNCM 1-2494 for the prevention, treatment and reduction of gastro-intestinal inflammation, in particular for the prevention and treatment of inflammatory bowel disease (IBD), ulcerative colitis (UC) and/or Crohn's Disease (CD).

According to one embodiment, the reduction of gastro-intestinal inflammation is defined as a reduction of the pro-inflammatory cytokine TNF-α in the colon. Hence, according to one embodiment, the invention is concerned with a method for the reduction of the pro-inflammatory cytokine TNF-α in the colon, comprising the step of administering to said subject an effective amount of the strain *Bifidobacterium animalis* subsp *lactis* DN-173010, deposited under the number CNCM 1-2494 or an effective amount of a fermented dairy product comprising the strain *Bifidobacterium animalis* subsp *lactis* DN-173010, deposited under the number CNCM 1-2494, in particular the Activia® product.

The term "administering" is intended to mean "'administering orally" i.e. that the subject will orally ingesting a bacteria according to the present invention or a composition comprising the bacteria according to the present invention, or is intended to mean "administering directly'* i.e. that a bacteria according to the present invention or a composition comprising the bacteria according to the present invention will be directly administered in situ, in particular by coloscopy, or rectally via suppositories.

Oral administration of the composition comprising the bacteria according to the present invention may be in the form of gelatin capsules, capsules, tablets, powders, granules or oral solutions or suspensions.

In a preferred embodiment of the invention, said composition is a food composition which can be used in the production of new foods or food ingredients as defined in EC Regulation No. 258/97, and in particular in the manufacture of functional foods. A food may be considered to be functional if it is demonstrated satisfactorily that it exerts a beneficial effect on one or more target functions in the organism, beyond the usual nutritional effects, improving the state of health and of well-being and/or reducing the risk of a disease.

In a preferred embodiment of the invention, said bacteria is administered in the form of a dairy product. In particular, the dairy product is a fermented dairy product and more particularly the fermented dairy product is a yoghurt.

Said composition may in particular constitute a probiotic package, for example, in the form of a capsule or a gelatin capsule.

The term "probiotics" is intended to mean dietary supplements containing potentially beneficial bacteria or yeasts. According to the currently adopted definition by FAO/WHO, probiotics are: 'Live microorganisms which when administered in adequate amounts confer a health benefit on the host". Lactic acid bacteria are the most common type of microbes used. Lactic acid bacteria have been used in the food industry for many years, because they are able to convert sugars (including lactose) and other carbohydrates into lactic acid. This not only provides the characteristic sour taste of fermented dairy foods such as yogurt, but also by lowering the pH may create fewer opportunities for spoilage organisms to grow, hence creating huge health benefits on preventing gastro-intestinal infections. Strains of the genera *Lactobacillus* and *Bifidobacterium* are the most widely used probiotic bacteria.

Probiotic bacterial cultures are intended to assist the body's naturally occurring gut flora to reestablish themselves. They are sometimes recommended by doctors, and, more frequently, by nutritionists, after a course of antibiotics, or as part of the treatment for gut related candidiasis. Claims are made that probiotics strengthen the immune system to combat allergies and other immunological diseases.

According to one embodiment, the subject is a mammal, preferably a human child, a human adult or a human elderly, most preferably a human adult.

According to one embodiment, the invention is concerned with a method for the prevention and treatment of irritable bowel syndrome (IBS). In gastroenterology, irritable bowel syndrome (IBS) or spastic colon is a functional bowel disorder characterized by abdominal pain and changes in bowel habits which are not associated with any abnormalities seen on routine clinical testing. It is fairly common and makes up 20-50% of visits to gastroenterologists. Lower abdominal pain, and bloating associated with alteration of bowel habits and abdominal discomfort relieved with defecation are the most frequent symptoms. It has to be understood for the good comprehension of the present invention that IBS is a syndrome and that under this expression are collected several symptoms observed on patients suffering from the gastro-intestinal area. Thus, there is not one disease (IBS) to treat but several types of diseases, and most of all, one or several symptoms to treat or decrease. According to one embodiment of the present invention, the method according to the invention is used for prevention and treatment of irritable bowel syndrome (IBS) wherein the IBS is related to, results from and/or is associated with gastro-intestinal inflammation, in particular gastro-intestinal micro-inflammation.

Concerning the several types of IBS, the abdominal pain type is usually described in a patient as either constipation-predominant (IBS-C) or diarrhoea-predominant (IBS-D), or a mixture of both (IBS-M) or none of these three characteristics (IBS-U; U means "'Unsubtype").

Preferably, the method according to the invention is for treating IBS-D (diarrhoea-predominant). Most preferably, the method according to the invention is for reducing gastro-intestinal inflammation of patients diagnosed as suffering from IBS-D.

Preferably, the method according to the invention is for treating subjects diagnosed according to ROME III criteria. Most preferably, the method according to the invention is for reducing gastro-intestinal inflammation of patients diagnosed as suffering from IBS-D, according to ROME III criteria.

ROME is a process developed to classify the functional gastro-intestinal disorders based on clinical symptoms. The term "ROME III* criteria" is intended to mean criteria for irritable bowel syndrome as follows: Recurrent abdominal pain or discomfort** at least 3 days per month in the last 3 months associated with 2 or more of the following:

* Criteria fulfilled for the last 3 months with symptom onset at least 6 months prior to diagnosis.

** "Discomfort" means an uncomfortable sensation not described as pain.

1. Improvement with defecation

2. Onset associated with a change in frequency of stool

3. Onset associated with a change in form (appearance) of stool

Other symptoms that are not essential but support the diagnosis of IBS:

Abnormal stool frequency (greater than 3 bowel movements/day or less than 3 bowel movements/week);

Abnormal stool form (lumpy/hard or loose/watery stool);

Abnormal stool passage (straining, urgency, or feeling of incomplete bowel movement);

Passage of mucus;

Bloating or feeling of abdominal distension.

Some or all of IBS symptoms can occur at the same time—some symptoms may be more pronounced than others.

All the criteria which are required to be diagnosed as IBS-D are described by the Rome III criteria (Longstreth et al., 2006).

The invention will now be further elucidated by several examples without being limited thereby.

It is understood that method claims may be alternatively formulated as second medical use claims (Composition for use), in particular in those jurisdictions where method claims are not allowed for grant of a patent; hence, such claims are implicitly disclosed herein.

EXAMPLES

Example 1

Figure 1:
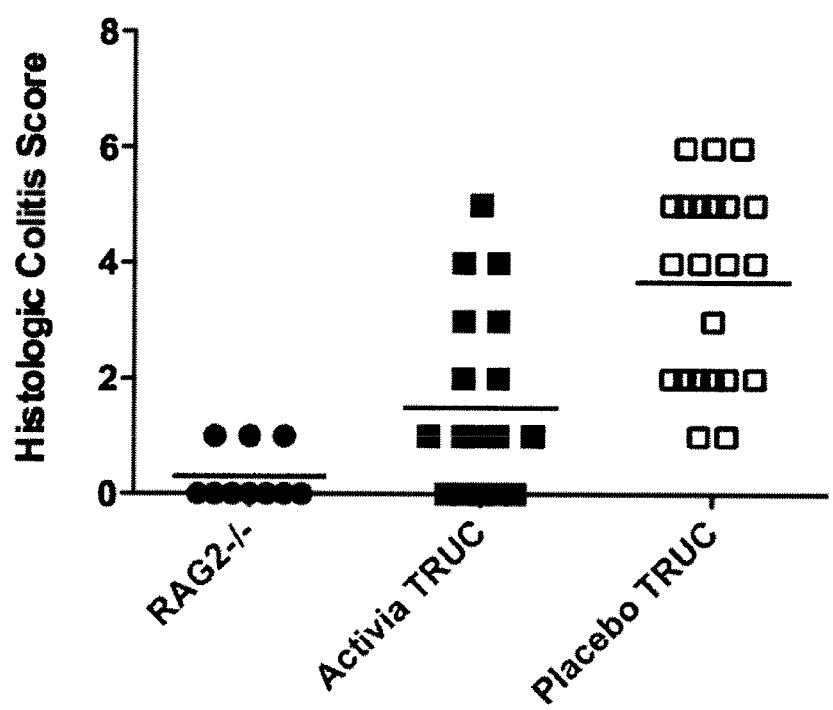
FIG. 1 Effect of 4 weeks consumption of Activia and placebo products on colitis score of TRUC mice and comparison with a control group (RAG2−/−)

Activia® Consumption Improves TRUC Colitis (FIG. 1)

Products

The test product was a fermented dairy product (Activia®, Danone Research, Palaiseau), comprising the probiotic strain *Bifidobacterium animalis* subsp *lactis* DN-173 010 (1.25×$10^{10}$ colony forming unit (cfu) per pot) together with the two classical yoghurt starter strains, *Streptococcus thermophilus* and *Lactobacillus bulgaricus* (1.2×10 cfu/pot). The test product was without flavour.

The control is a milk-based non-fermented dairy product without probiotics and with low content of lactose <4 g/pot as in the test product (acidified milk).

Product Intervention

TRUC mice (n=20) at 4 weeks of age were fed either with the test product (n=10) or with a control product (non-fermented acidified milk) (n=10) daily over a four week period.

Microbial Analysis

Feces of TRUC mice before and after supplementation (4 and 8 weeks of age, respectively) as well as of 10 control mice (RAG2−/−) were collected. Fecal DNA or RNA was extracted and qPCR was performed to quantify different bacterial taxonomic groups.

Histological Colitis Score

Colonic inflammation was assessed by histological analysis at the end of supplementation (8 weeks of age) by a pathologist blinded to the genotype and treatment intervention.

Results

Activia® was shown to ameliorate TRUC colitis.

Example 2

Figure 2:
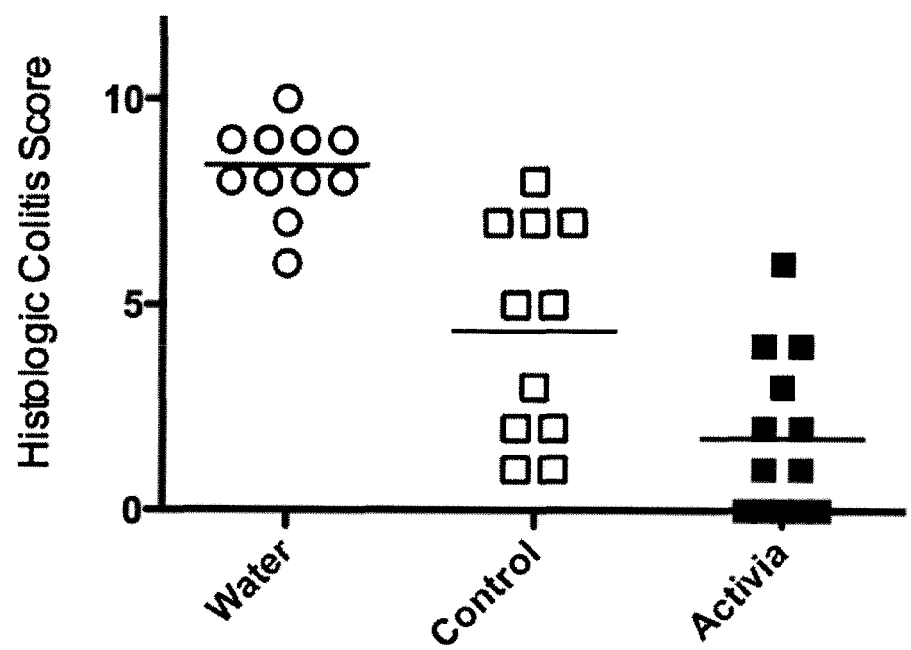
FIG. 2 Effect of 4 weeks consumption of Activia, a placebo product and water on colitis score of TRUC mice FIG. 3 Effect of 4 weeks administration of living culture of *B. lactis* at different age (4, 8 and 12 weeks) and compared with administration of the culture medium (MRS) alone.

Non Bacterial Products in Activia Improve TRUC Colitis (FIG. 2)

Experimental:

see above—Outcome measure: Histological colitis score.

Example 2

Figure 3:
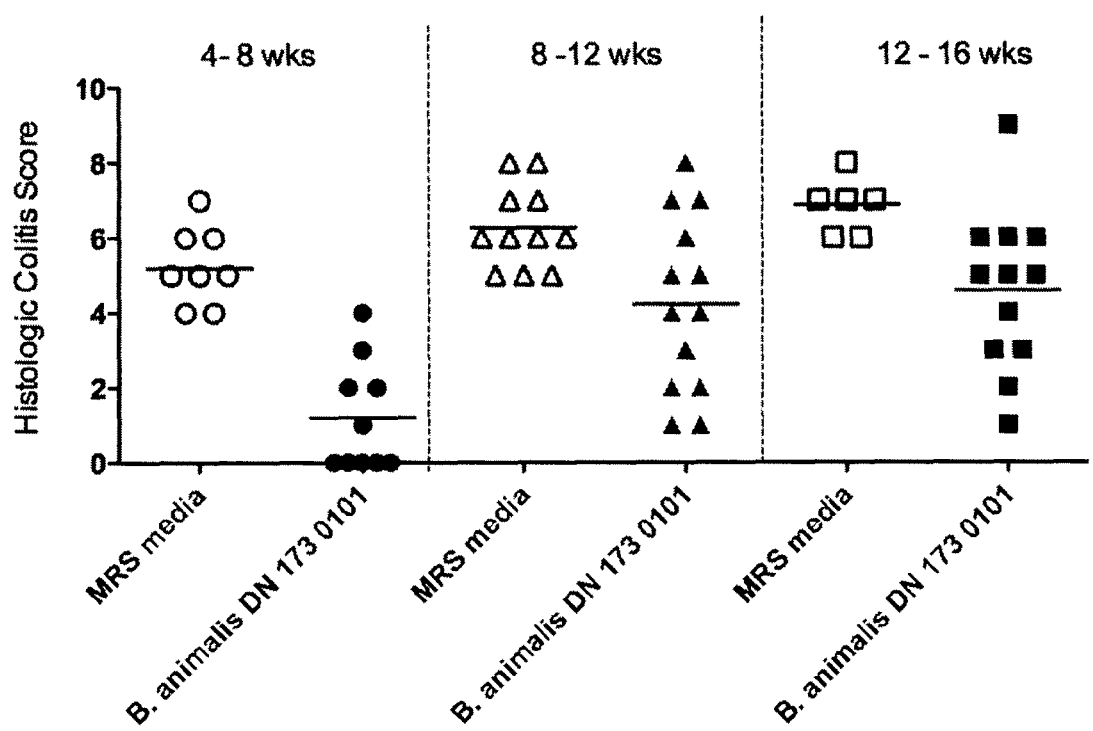

*Bifidobacterium Animalis* Subsp *Lactis* 173 010B Improves TRUC Colitis (FIG. 3)

Experimental

Experimental: *Bifidobacterium animalis lactis* 173 010 was grown overnight in MRS medium and a bacterial population of 4-5×$10^8$ cfu was collected from this culture and then administrated daily during 4 weeks to BALB/c TRUC mice aged of 4 (n=10), 8 (n=15) or 12 (n=15) weeks. As a control, the same volume of MRS medium alone was administrated in the same manner as the living culture.

Histological Colitis Score

Colonic inflammation was assessed by histological analysis at the end of supplementation by a pathologist blinded to the genotype and treatment intervention.

Results

The probiotic strain from Activia® *B. animalis lactis* DN 173 010B impacts on TRUC colitis severity but not to the same extent as Activia®. The effect of the 173 010B strain is visible across the TRUC disease course, either at early or late points. These results suggest that the effect of Activia® on TRUC colitis can't be reduced to the effect of 173 010B strain alone. Other components/characteristics of this dairy product impact also on TRUC colitis.

Example 4

Activia® Consumption Reduces Inflammation in TRUC Mice

Figure 4:
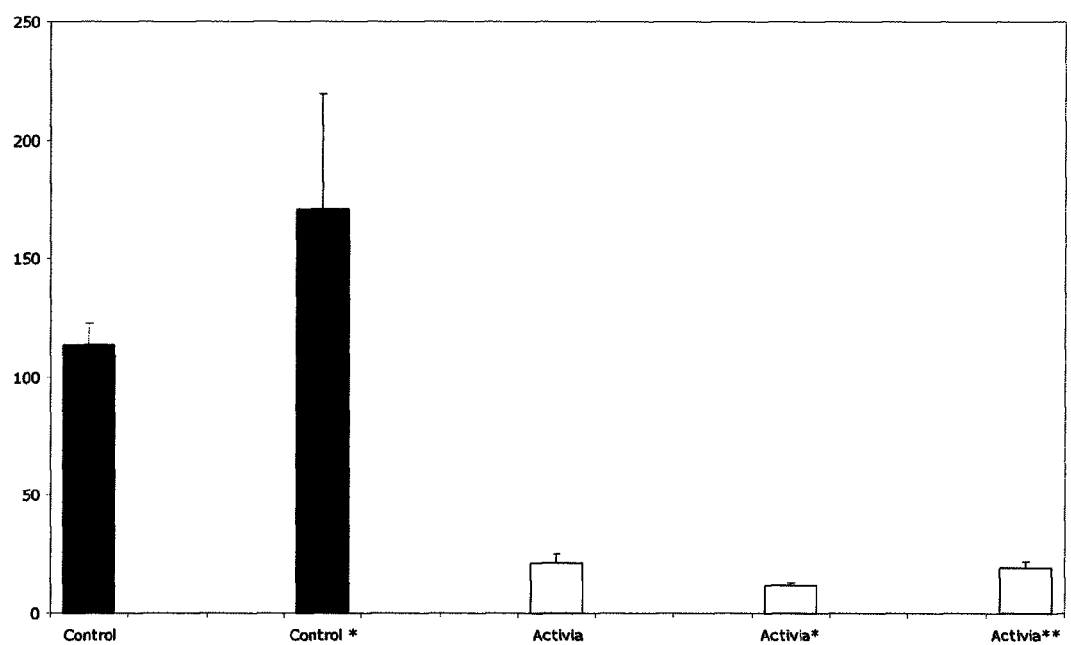
FIG. 4 Effect of 4 weeks consumption of Activia and placebo products on the pro-inflammatory cytokine TNF-α in the colon.

Activia® reduces the excessive production of the pro-inflammatory cytokine TNF-α in the colon (FIG. 4).

Experimental:

see above—Outcome measure: colonic TNF-α level (pg/ml)

CONCLUSIONS

The gut microbiota is essential for the generation of ulcerative colitis (UC) which spontaneously occurs in T-bet RAG2 deficient (TRUC) mice (Garrett et al.). In this model of gut inflammation, microbial modulation in response to antibiotic therapy leads to improvement of UC scores. This raises the possibility that other means of gut microbiota manipulation, in particular food interventions, may also impact the inflammation in this model. The aim of this study was to determine the microbial structure of the gut microbiota of TRUC mice and to test the impact of foods containing living bacteria on chronic gastro-intestinal inflammation. The effects of the nutritional intervention were assessed by i) colon histology and ii) gut microbiota quantitative analysis.

Mapping the gut microbiota by real time qPCR analysis of stool samples from TRUC and RAG2−/− (control) mice revealed significant differences in bacterial populations, including a dramatic reduction of bifidobacteria in TRUC. To test whether a fermented milk containing live bifidobacteria, would improve colitis in this model, TRUC mice consumed either a fermented-milk containing *Bifidobacterium animalis* subsp *lactis* DN-173010B or a control product (non-fermented acidified milk) over a 4-week period. Interestingly, the consumption of the test product showed a significant decrease in gut inflammation as demonstrated by histology and indeed coincided with alterations in the gut microbiota. The results show that consumption of fermented milk containing *Bifidobacterium animalis* subsp *lactis* s DN-173010 is able to decrease UC, potentially by direct immune effects or by creating unfavorable conditions for putative pathogenic bacteria that may be implicated in disease progression in this animal model.

The invention claimed is:

1. A method for treating inflammatory bowel disease (IBD), ulcerative colitis (UC) and/or Crohn's Disease (CD) in a subject in need thereof, comprising the step of administering to said subject an effective amount of the bacterial strain *Bifidobacterium animalis* subsp *lactis* DN-173010, deposited under the number CNCM 1-2494.

2. A method for treating inflammatory bowel disease (IBD), ulcerative colitis (UC) and/or Crohn's Disease (CD) in a subject in need thereof, comprising the step of administering to said subject an effective amount of a fermented dairy product comprising the bacterial strain *Bifidobacterium animalis* subsp *lactis* DN-173010, deposited under the number CNCM 1-2494.

3. A method according to claim 2, wherein the product further comprises the lactic acid bacteria *Streptococcus thermophilus* and *Lactobacillus bulgaricus*.

4. A method according to claim 1 wherein the bacterial strain *Bifidobacterium animalis* subsp *lactis* DN-173010, deposited under the number CNCM 1-2494 is administered during at least 14 days.

5. A method according to claim 1, wherein about between $10^3$ and $10^{12}$ cfu of said bacterial strain is administered to the subject per intake.

6. A method according to claim 5, wherein between $10^3$ and $10^{12}$ cfu of said bacterial strain is administered to the subject two times per day during at least 28 days.

7. A method according to claim 1, wherein said bacterial strain is administered in the form of a pharmaceutical composition.

8. A method according to claim 1, wherein the fermented dairy product is a yoghurt.

9. A method according to claim 1, wherein said subject is a mammal, preferably a human adult.

10. A method according to claim 2 wherein the bacterial strain *Bifidobacterium animalis* subsp *lactis* DN-173010, deposited under the number CNCM 1-2494 is administered during at least 14 days.

11. A method according to claim 3 wherein the bacterial strain *Bifidobacterium animalis* subsp lactis DN-173010, deposited under the number CNCM 1-2494 is administered during at least 14 days.

12. A method according to claim 2, wherein about between $10^3$ and $10^{12}$ cfu of said bacterial strain is administered to the subject per intake.

13. A method according to claim 3, wherein about between $10^3$ and $10^{12}$ cfu of said bacterial strain is administered to the subject per intake.

14. A method according to claim 2, wherein said bacterial strain is administered in the form of a pharmaceutical composition.

15. A method according to claim 2, wherein the fermented dairy product is a yoghurt.

* * * * *